US011612705B2

(12) United States Patent
Gründler et al.

(10) Patent No.: US 11,612,705 B2
(45) Date of Patent: Mar. 28, 2023

(54) SYSTEM FOR ASSISTING BREATHING AND A PATIENT SET THEREFOR

(71) Applicant: GRÜNDLER GMBH, Freudenstadt (DE)

(72) Inventors: Markus Gründler, Freudenstadt (DE); Christoph Gründler, Freudenstadt (DE); Bernd Reslo, Reichling (DE); Thilo Joost, Friedberg (DE); Rainer Köbrich, Neulußheim (DE)

(73) Assignee: GRÜNDLER GMBH, Freudenstadt (DE)

( * ) Notice: Subject to any disclaimer, the term of this patent is extended or adjusted under 35 U.S.C. 154(b) by 454 days.

(21) Appl. No.: 16/628,996

(22) PCT Filed: Jul. 11, 2018

(86) PCT No.: PCT/DE2018/000215
§ 371 (c)(1),
(2) Date: Jan. 6, 2020

(87) PCT Pub. No.: WO2019/011365
PCT Pub. Date: Jan. 17, 2019

(65) Prior Publication Data
US 2020/0121872 A1  Apr. 23, 2020

(30) Foreign Application Priority Data

Jul. 13, 2017  (DE) ..................... 10 2017 006 655.8

(51) Int. Cl.
*A61M 16/00* (2006.01)
*A61M 16/08* (2006.01)
*A61M 16/04* (2006.01)

(52) U.S. Cl.
CPC .... *A61M 16/0003* (2014.02); *A61M 16/0072* (2013.01); *A61M 16/022* (2017.08);
(Continued)

(58) Field of Classification Search
CPC .......... A61M 16/0072; A61M 16/0075; A61M 16/0078; A61M 16/00–0012; A61M 16/0045–0081
See application file for complete search history.

(56) References Cited

U.S. PATENT DOCUMENTS 3,695,263 A * 10/1972 Kipling ................. A61M 16/00
128/204.24
6,041,777 A * 3/2000 Faithfull ........... A61M 16/0054
128/200.24
(Continued)

FOREIGN PATENT DOCUMENTS

DE        929 637         6/1955
DE     43 12510 A1       10/1993
(Continued)

OTHER PUBLICATIONS

International Preliminary report on Patentability dated Jan. 14, 2020 and translation of the Written Opinion of the International Searching Authority dated Oct. 31, 2018 for corresponding International Application No. PCT/DE2018/000215.
(Continued)

Primary Examiner — Joseph D. Boecker
Assistant Examiner — Thomas W Greig
(74) Attorney, Agent, or Firm — Renner, Otto, Boisselle & Sklar, LLP

(57) ABSTRACT

A system for supporting pulmonary gas exchange in patients and for coupling to a ventilating system or for use in the case of non-ventilated patients, which has a flexible hose introducible into the trachea of a patient, a pump unit, a reservoir unit and a controller such that via the flexible hose and by means of the pump unit it is possible to regulate aspiration, especially end-expiratory aspiration, and recirculation, especially end-inspiratory recirculation, of the aspirated gas. In
(Continued)

order that the system can be operated independently of a ventilating system, the system has a sensor.

16 Claims, 5 Drawing Sheets

(52) U.S. Cl.
CPC ........ *A61M 16/04* (2013.01); *A61M 16/0841* (2014.02); *A61M 2016/0027* (2013.01); *A61M 2205/502* (2013.01); *A61M 2230/42* (2013.01); *A61M 2230/432* (2013.01)

(56) References Cited

U.S. PATENT DOCUMENTS

| | | | | |
|---|---|---|---|---|
| 6,196,222 | B1 * | 3/2001 | Heinonen | A61M 16/12 128/204.23 |
| 7,335,164 | B2 * | 2/2008 | Mace | A61B 5/083 73/23.3 |
| 8,480,624 | B2 * | 7/2013 | Kim | A61M 5/2053 604/71 |
| 2003/0131665 | A1 * | 7/2003 | Ahlmen | A61M 16/0072 73/700 |
| 2004/0182391 | A1 | 9/2004 | Hallback | |
| 2004/0211423 | A1 * | 10/2004 | Baecke | A61M 16/024 128/204.23 |
| 2007/0062535 | A1 | 3/2007 | Psaros | |
| 2008/0072911 | A1 * | 3/2008 | Flagler | A61M 16/0875 128/207.14 |
| 2012/0283592 | A1 * | 11/2012 | Schuessler | A61M 16/0006 128/204.23 |
| 2014/0005566 | A1 * | 1/2014 | Homuth | A61M 16/01 128/204.23 |
| 2016/0114113 | A1 | 4/2016 | Homuth et al. | |
| 2019/0134331 | A1 * | 5/2019 | Meyer | A61M 16/026 |

FOREIGN PATENT DOCUMENTS

| | | |
|---|---|---|
| DE | 10337138 A1 | 3/2005 |
| DE | 60 2004 003 409 T2 | 10/2007 |
| EP | 1329238 A1 | 7/2003 |
| EP | 1459778 A1 | 9/2004 |
| WO | 91/19526 | 12/1991 |
| WO | WO-2012062266 A1 * | 5/2012 ............ A61M 16/00 |

OTHER PUBLICATIONS

International Search Report for corresponding International Application No. PCT/DE2018/000215, dated Oct. 31, 2018.
Search Report for corresponding DE Application No. 10 2017 006 655.8 dated Jul. 14, 2018.

* cited by examiner

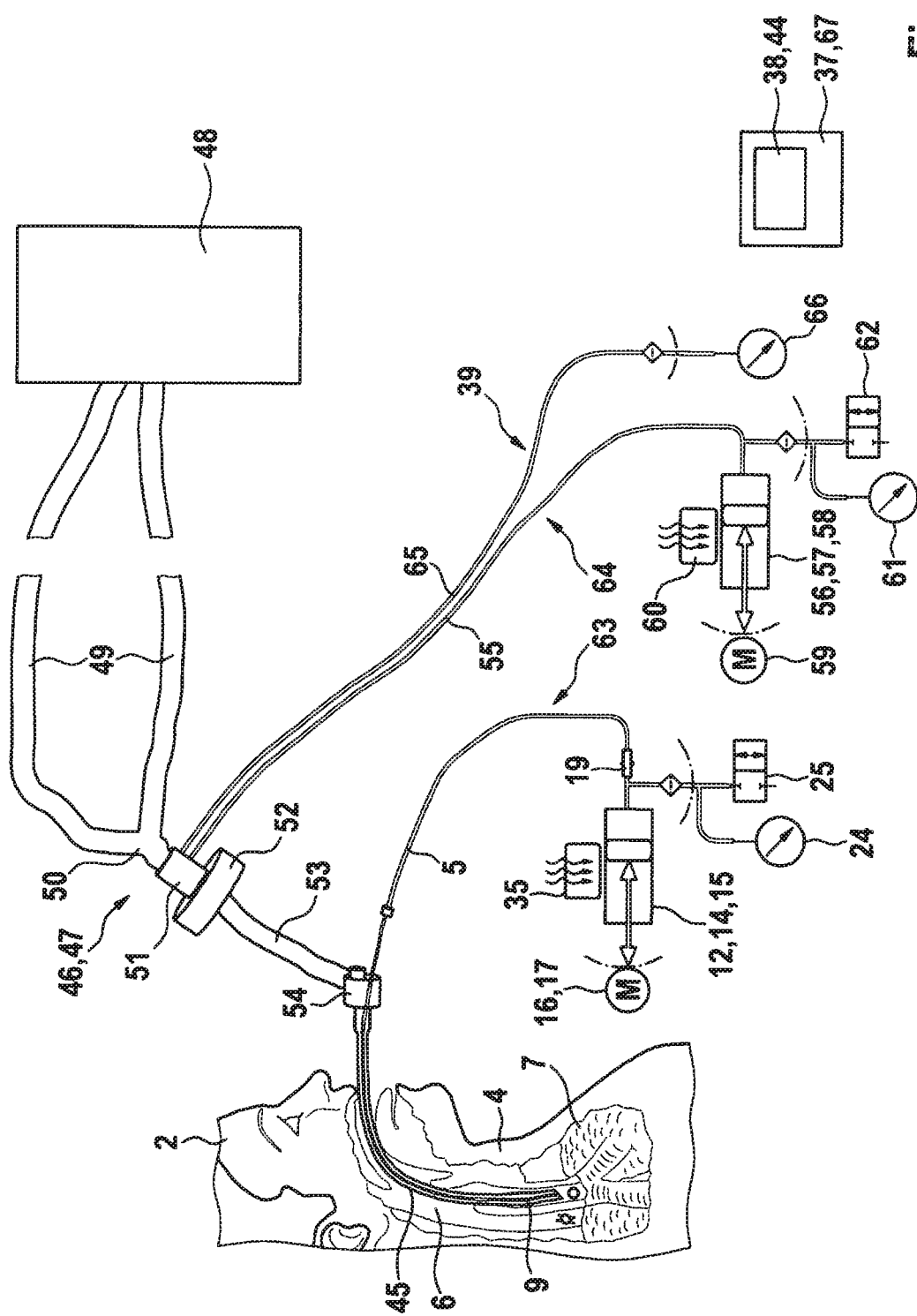

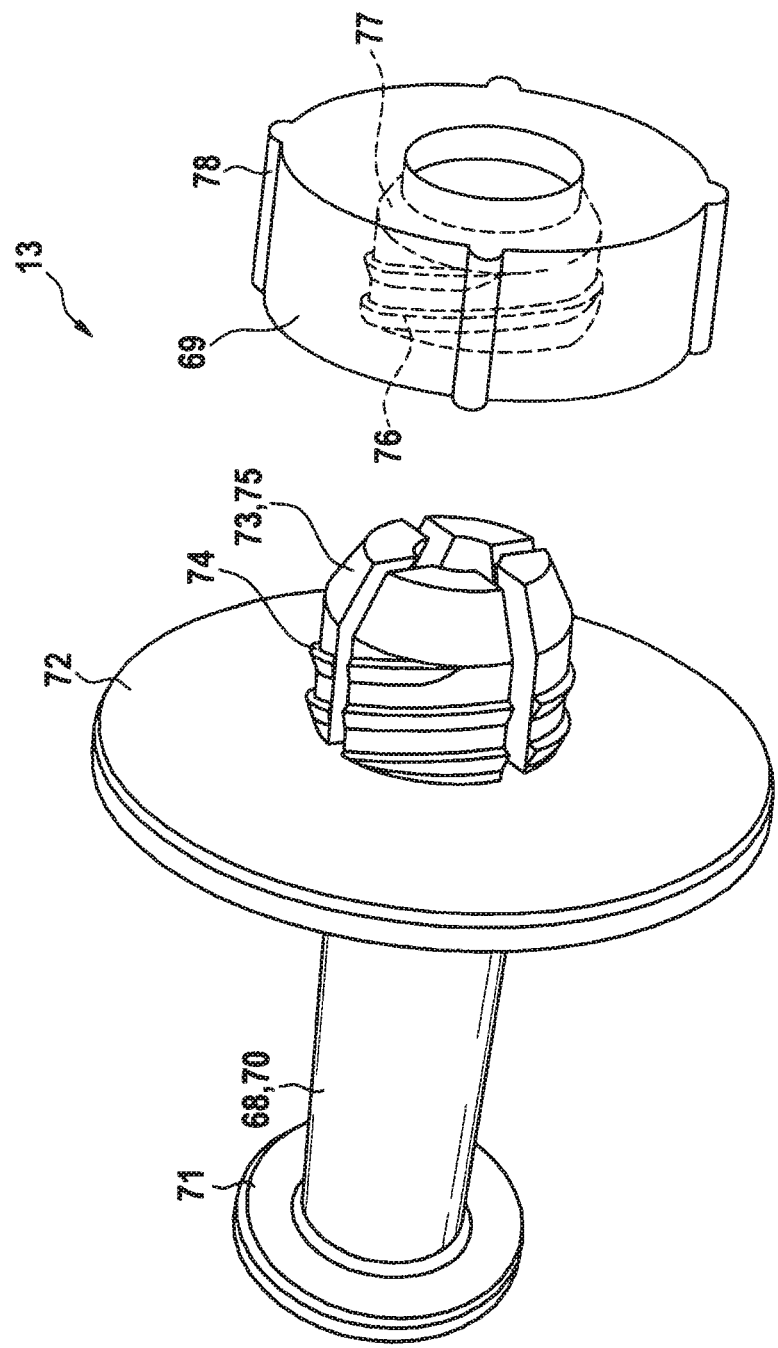

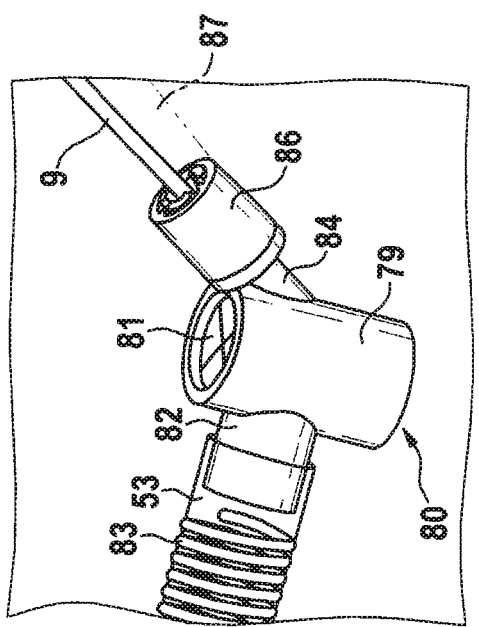
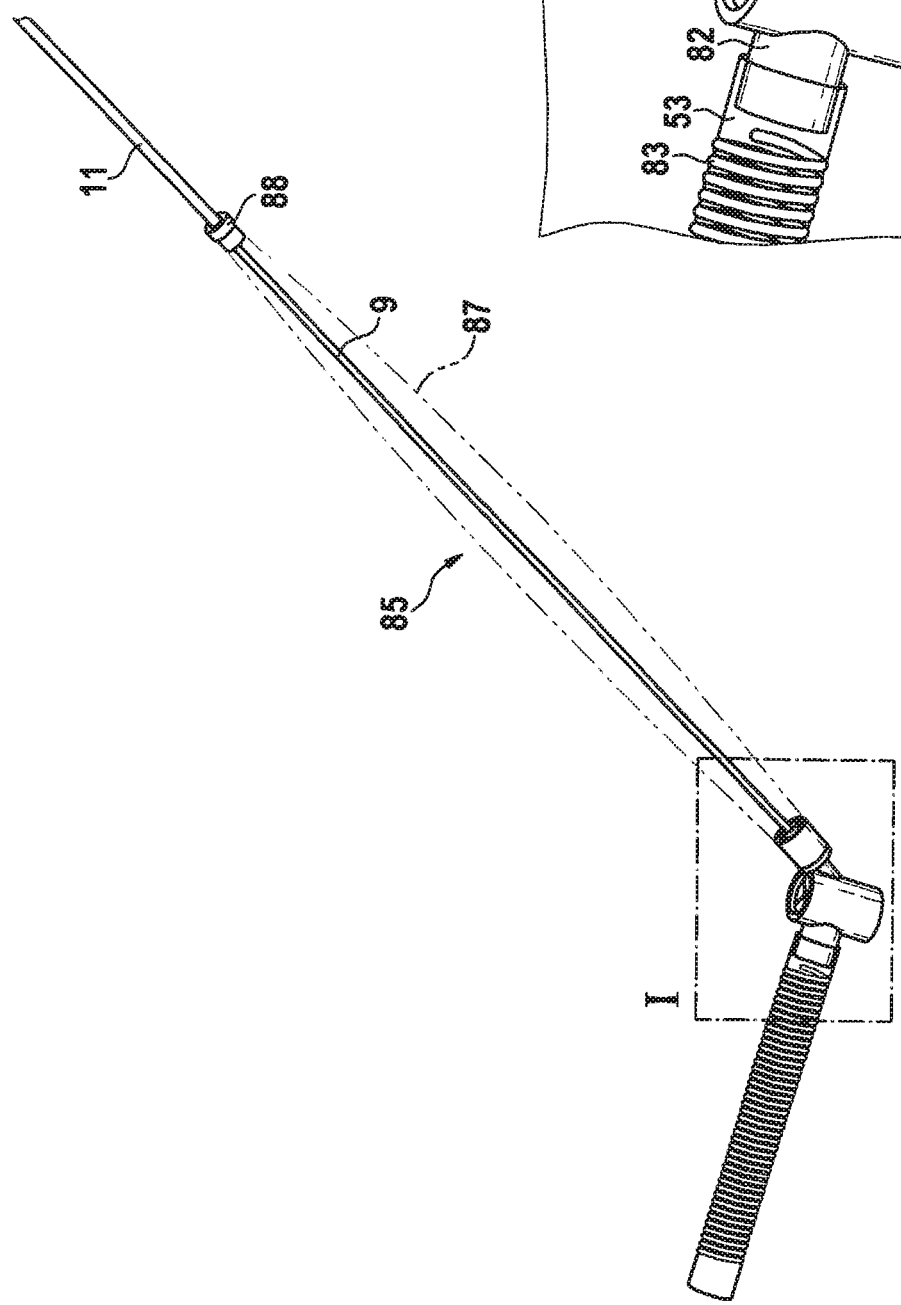

SYSTEM FOR ASSISTING BREATHING AND A PATIENT SET THEREFOR

TECHNICAL FIELD OF THE INVENTION

The invention relates to a system for supporting pulmonary gas exchange in patients and to a patient set therefor.

DESCRIPTION OF THE RELATED ART

Artificial ventilation is long-established in the case of respiratory disorders. During artificial ventilation the breathing gas is usually delivered to the airways cyclically by means of elevated pressure via a hose introduced into the trachea or by means of a face mask, while exhalation takes place automatically as a result of the passive restoring forces of the breathing apparatus when the external elevated pressure is reduced. To prevent injuries being caused by high ventilation pressures, efforts are made to keep the tidal volume and the ventilation pressures during ventilation as low as possible. This is always subject to the limiting effect of what is known as the "oscillating volume" or "dead space volume" which is moved bidirectionally in the air-conducting system of patient and ventilating system. The exhaled volume remaining in the oscillating volume is re-inhaled when the subsequent breath is taken and therefore the proportion of fresh air decreases as the oscillating volume fraction increases. The greater the dead space volume in relation to the tidal volume, the more ineffective is the gas exchange.

The publication DE 60 2004 003 409 T2 discloses a system which is coupled as a support system to a ventilating system. The ventilating system has a patient line which extends from a Y-piece into the trachea of a patient. By means of an aspiration line of the support system, which is connected to the patient line, exhaled gas is aspirated from the patient line during the end phase of exhalation. At the same time, at another location closer to the ventilator, fresh gas is supplied to the inspiration line through a further line in order not to disturb the functioning of the ventilating system. The dead space volume formed by the patient line is therefore partially freed of exhaled air. Accordingly, during subsequent inhalation less exhaled gas, but rather fresh gas, is re-inhaled. The aspirated gas is supplied to the patient line again at the beginning of the next exhalation.

That known system, however, can be operated only when closely coupled to a ventilating system, because the support system is controlled on the basis of the signals of the ventilating system, especially signals relating to the flow/time ratio. Since there are no standard interfaces for such signals, a specific interface between the support system and the ventilating system must be created in each case. Furthermore, the known system is susceptible to blockages of the aspiration line, so that reliable supporting of the ventilating system is not ensured.

The problem underlying the invention is therefore to provide a system for supporting pulmonary gas exchange in patients which provides reliable supporting of the patient's breathing, especially without signal-based coupling to the ventilating system.

SUMMARY OF THE INVENTION

The system according to the invention serves for supporting pulmonary gas exchange in patients and for coupling to a ventilating system or for use in the case of non-ventilated patients. The system has a flexible hose which is introducible into the trachea of a patient, especially as far as the distal trachea or the primary bronchi, it being possible for the hose to have been introduced into the trachea through a surgically created access point, especially in the throat region, or through the mouth or nose. Especially in the case of a patient being ventilated by a ventilating system, the flexible hose can be introduced into the trachea through an endotracheal tube or a tracheal cannula of the ventilating system or can be integrated into the endotracheal tube or the tracheal cannula. Furthermore, the system has a pump unit and a reservoir unit. The pump unit serves to aspirate gas from the lung, from the trachea or from the line system of a ventilator and to return it again by pumping, this also being referred to as "recirculation" hereinbelow. The reservoir unit serves for intermediate storage of the aspirated gas before it is returned again. The intermediate storage can also be utilised for controlling the temperature of the gas. The pump unit and the reservoir unit preferably form a common unit and are especially implemented in the form of a piston pump. Furthermore, the system has a controller such that via the flexible hose and by means of the pump unit it is possible to regulate aspiration and recirculation of the aspirated gas. The aspiration is effected especially expiratorily and especially end-expiratorily, while the recirculation is effected especially late-inspiratorily. This facilitates the above-described effect of reducing the dead space volume, because during inhalation the proportion of rebreathed spent breathing gases is reduced. Consequently the partial pressure differentials between the blood side and the gas side in the lung are increased, resulting in an improvement in oxygenation and in increased elimination of respirable substances, for example $CO_2$ or alcohol. "Recirculation" means at least partial return to the patient, this especially being effected through the flexible hose through which the aspiration has previously taken place.

The system is characterised in that it has a sensor, especially a sensor for determining the pressure, the flow velocity and/or the composition of a gas. The sensor provides a simple way of determining data relating to the state of the system or the condition of the patient and, as a result, especially of identifying changes on the part of the patient, such as, for example, a change in breathing rhythm and/or disruptions, such as blockage of the flexible hose. Picking up the signal of a sensor on or in the patient or in the region of the flexible hose can serve for obtaining information relating to the activity of a ventilating system with which the system is pneumatically coupled, so that a data interface between the two systems is unnecessary. The data from the sensor can serve for adaptation to the patient and/or to the ventilator or can be the basis for eliminating a disruption, whether it be caused by an operator or by the system itself. In particular, the system has a device for counteracting a blockage in the flexible hose in dependence upon data from the sensor.

Preferably the sensor is arranged between an open, patient-side end of the flexible hose and the reservoir unit in respect of the flow of the gas conducted by the system. Alternatively the sensor could be arranged in the reservoir unit itself, but this gives rise to a more complicated structure. "Between" does not mean here that flow needs to pass through the sensor itself; the sensor can also be arranged on a branch line.

In order to minimise blockages in the flexible hose as well as adhesion by suction, the invention proposes to equip such a flexible hose, at its patient-side open end, preferably with a plurality of lateral openings arranged on the circumference—comparable to atraumatic aspiration catheters. Preferably such holes are protected from coughed-up secretions etc. geometrically by means of small projections/baffles.

In order to be able to detect blockages in the system, especially in the flexible hose, the invention proposes that the sensor is a high-pressure sensor and is configured and arranged in such a way that it is able to detect the fluctuations in pressure generated by the pump unit. A blockage or a leakage can be inferred by way of the amplitude and form of the pressure fluctuations, that is to say, during suction, by a significantly lower pressure or slower pressure equalisation than in the case of earlier suction operations and, during return, by a significantly higher pressure or slower pressure equalisation. A high-pressure sensor is especially suitable if it has a time resolution sufficient for the said function, a sufficient measuring range and a sufficient measuring accuracy in the relevant pressure range. In particular, the resolution is 1 mbar or less within a pressure range of at least +/−750 mbar, with a time resolution of at least 25 readings per second.

Preferably the system has a high-resolution pressure sensor for detecting the fluctuations in pressure in the flexible hose generated by spontaneous breathing activities of the patient. The high-resolution pressure sensor can be the sensor mentioned above but it is especially an additional sensor. There is therefore especially a high-pressure sensor and a high-resolution pressure sensor. The high-resolution pressure sensor enables the system to be used in a non-ventilated patient. As long as the pump unit is not operating, the pressure in the flexible hose is substantially the same as in the trachea of the patient. The data from the high-resolution pressure sensor can accordingly be used to infer the breathing activity of the patient, that is to say to detect at what point in the breathing cycle the patient currently is and with what intensity breathing is taking place. The high-resolution pressure sensor is suitable for that purpose if it has a time resolution sufficient for the said function, a sufficient measuring range and a sufficient measuring accuracy in the relevant pressure range. In particular, the resolution is 0.1 mbar or less within a pressure range of at least +/−5 mbar, with a time resolution of at least 25 readings per second. If the high-resolution pressure sensor is liable to be damaged by higher pressures, such as may occur, for example, during coughing and speaking, it should be protected in a suitable way, preferably by a sensor protection valve. Because the breathing activity of the patient can be detected with the high-resolution pressure sensor, the system is suitable for use for supporting breathing without further apparatus, that is to say especially in the case of patients who are not being ventilated by a ventilating system. Supporting spontaneous breathing by reducing the above-described adverse effect of the dead space volume is a very effective aid in respiratory failure, but the use of the system is, above all, less traumatic than ventilation by means of a ventilating system, which can create unnatural and potentially damaging pressure conditions in the airways. As long as the patient is able to breath spontaneously, the use of the system can make it unnecessary to employ escalating treatment methods, such as, for example, non-invasive or invasive ventilation and/or an extracorporeal gas exchange procedure (artificial lung or heart/lung machine). At the same time, the system does not conflict with ventilation by means of a ventilating system, but can be operated in interaction with or instead of the ventilating system.

Preferably the system has a switchable supply line through which a volumetric flow of a further gas can be conducted to the flexible hose instead of or in addition to the recirculated gas. "Switchable" here means that a fluidic connection can be opened and closed. The supply of a further gas broadens the range of therapeutic treatments that are possible using the system. "Further gas" here means pure gases, such as, for example, oxygen, helium, NO or $CO_2$, but also mixtures thereof, for example air. In particular, oxygenation can be significantly assisted by the targeted supply of oxygen. The supply of further gases is effected especially in dependence upon the partial pressures in the blood or upon further measured values, such as the oxygen saturation, which can be detected by further sensors, especially by sensors which are not part of the system and are coupled via an interface. The supply of $CO_2$ especially makes it possible to carry out isocapnic hyperventilation, which is an established procedure, for example for the treatment of carbon monoxide poisoning.

The flexible hose preferably has a first hose section for introduction into the trachea and a second hose section for connection of the first hose section to the reservoir unit with a larger external cross-section. By means of the thinner, first hose section it is possible to carry out aspiration from or introduction into the trachea in a way that is less traumatic for the patient, while flow conditions are disrupted only to a minimal extent by the small diameter, and the second hose section allows a larger internal cross-section and accordingly allows transport of gas with smaller, line-related pressure losses.

In order that the system can be used for supporting the ventilating system in the case of a ventilated patient, the invention proposes that a further flexible hose, a further pump unit and a further reservoir unit be provided for aspirating and recirculating gas from the line system of the ventilating system. There are accordingly two pathways, each consisting of a flexible hose, a pump unit and a reservoir unit. Both pathways are especially controlled by the controller. One pathway can aspirate breathing air from the trachea and return at least some of that gas to the trachea again, as described above, and another pathway can aspirate gas from the line system of the ventilating system and return it again. In particular, the two pathways are controlled so that essentially one pathway aspirates while the other returns. This has the considerable advantage that, in the region of the ventilating system, there are no disruptive changes in the pressure profiles and flow profiles through the system. In respect of the ventilating system, the system according to the invention therefore remains "invisible" and the ventilating system can be operated without requiring adaptation.

Preferably a separate sensor line is provided which is coupled-in pneumatically in the region of the Y-piece of the ventilator. As a result, the status and activity of the ventilator in relation to the patient can at any time be monitored and taken into consideration in the controller. Such a sensor line can consist of a plurality of mutually separate lumina and, by being arranged on different sides of a flow obstruction in the gas stream, provide information about the level, direction and variation over time of gas flows.

Preferably the two pump units are controllable independently of one another by the controller. In particular, they are not mechanically rigidly coupled. By virtue of the independent actuation it is possible to compensate for the inertia of the entire system consisting of ventilating system and system, which inertia results especially from the compressibility of the gas and the flow resistances. In particular, the pumping and the aspiration take place slightly staggered in time and with different velocity profiles. As a result, in particular disruptive changes in pressure in the line system of the ventilating system caused by the aspiration in the lung-side pathway can be prevented, for example by advancing the time at which gas is pumped in through the other pathway or by pumping in the gas at a higher velocity. Reduced pressure in the line system during such end-expiratory dead space aspiration, or a resultant flow of gas out of the ventilating system in the direction of the patient, could suggest inhalation to the ventilating system, which would disrupt the functioning of the ventilating system.

In a preferred embodiment, the system has a gas analysis sensor, especially a $CO_2$ sensor. This allows permanent monitoring of the efficiency of the system and of the condition of the patient, because with each aspirating operation an analysis of the exhaled gas can be carried out. Such monitoring can serve on the one hand for controlling the system and on the other hand for indicating the condition of the patient to an attending physician. The gas analysis sensor is arranged between an open, patient-side end of the flexible hose and the reservoir unit in respect of the flow of aspirated gas.

The aspiration, intermediate storage and recirculation of the breathing gas can give rise to an undesirable change in temperature. The invention therefore proposes that the flexible hose and/or the reservoir unit be encased in thermal insulation and/or have a temperature-control unit. The temperature-control unit is especially a heating unit.

As mentioned, blockage of the gas-conducting components, especially of the flexible hose, by bodily secretions of the patient and the like cannot be ruled out. The sensor, especially the high-pressure sensor mentioned above, can serve to detect such disruption. In order to be able to counteract that disruption, especially automatically, the invention proposes that the system has a junction with a switchable opening to the environment such that, by means of the pump unit, air can be drawn in from the environment for blowing out the flexible hose. The opening to the environment can be protected against penetration of pathogens and contaminants using a filter. The switchable opening can alternatively also be utilised for connection of ventilation gases instead of ambient air, as described above for the switchable supply line. The switchable opening can equally also serve as emergency venting in the event of undesirable elevated pressure.

In order to support isocapnic hyperventilation it would be possible, for example, to connect the switchable opening of the second pathway to a source of compressed $CO_2$ gas.

Preferably the pump unit is intended to be couplable to and separable from a drive unit for the pump unit by the user without tools. This makes it possible for the pump unit to be made ready or replaced by a fresh pump unit on changing from one patient to the next, while the drive unit can be re-used immediately. The tool-free couplability especially allows quick and easy changing of the pump unit.

The invention also proposes that the system has a communication interface for cable-connected or wireless exchange of information with third-party devices, with external sensors and/or with remote monitoring systems. For example, a further sensor, such as a transcutaneous $CO_2$ sensor and/or a blood gas analysis device, can either be incorporated into the controller or an existing output unit of the controller can be utilised to display the readings of the further sensor.

Preferably the system has a grommet for passing-through and fixing of the flexible hose, especially in the case of a spontaneously breathing non-ventilated patient. After surgical creation of an opening into the trachea from the outside, the grommet can be introduced into that opening in order to keep the opening open, even if the flexible hose has not been passed through that grommet. Should the patient not need the system or if the patient is temporarily being ventilated by means of a ventilating system, the opening does not close up but is kept open by the grommet. The grommet is especially ring-shaped. Preferably the system has a stopper for closing the grommet when there is no flexible hose passing through it. Furthermore, the grommet especially has a clamping device for securing the introduced flexible hose in the desired position against slippage. Its position can be checked by applied markings and by visibility in imaging procedures (for example X-ray).

The controller is preferably configured so that, in dependence upon data from the sensor and/or inputs via a user interface, closed-loop control and/or an output with at least one of the following output variables takes place: timepoint of the pumping and/or aspiration, velocity profile of the pumping and/or aspiration, pumped and/or aspirated volume. The objective here is always that there should be no disruption or only minimal disruption of the breathing/ventilation of the patient. "Closed-loop control" means that a closed-loop circuit is formed, while "output" means that pure open-loop control takes place, without a closed-loop circuit being formed.

The determination of the beginning of aspiration is especially effected in dependence upon the measured beginning of expiration and the expected end of expiration. The beginning of expiration can be detected by measurement of a significant fall in the pressure in the region of the flexible hose between aspiration and pumping, or by a separate sensor. Alternatively or in addition, the determination of the beginning of aspiration can be effected by analysis of the variation in pressure over time, that is to say the change in pressure, in the region of the flexible hose. On exhalation the pressure drops, that is to say in this case the change in pressure is a fall in pressure, the fall in pressure per unit time becoming ever smaller, that is to say the first derivative of the pressure with respect to time is negative and the second derivative positive. The beginning of aspiration can take place by taking into account a threshold value for the fall in pressure (first derivative of the pressure with respect to time). The aspiration is optionally started after a defined delay if the fall in pressure drops below a threshold value, which is equivalent to exceeding a specific value of the first derivative of the pressure with respect to time.

A further signal that can be used for timepoint control is the pressure differential between different measuring points and their rate of change over time. For example, a higher pressure in the flexible hose of the pathway at the trachea in comparison with the pressure in the flexible hose of the pathway at the line system of the ventilator is a measure of exhalation flow. The injection of the spent gas is accordingly effected when there is essentially no longer a flow of gas, that is to say no longer a pressure gradient, in the direction of the patient or when that flow of gas is just about to reverse as an indicator of the beginning of expiration.

Preferably the controller has a program for optimising the aspiration timepoint, which accordingly means the start of aspiration. The objective here is as late as possible aspiration within the expiration, because in that phase the $CO_2$ concentration is at a maximum and accordingly the methodology of the dead space aspiration is at its most effective. How well this is achieved is described by what is known as "synchronisation". However, the aspiration must be interrupted prematurely if the patient inhales earlier than expected by the system, that is to say while aspiration is still taking place. The optimisation program detects an increased incidence of such interruptions and if necessary adapts the aspiration timepoint by advancing that timepoint, which can also be effected stepwise. The increased incidence of interruptions signifies poor synchronisation. Conversely, if there are no interruptions the program can move the aspiration timepoint back in time in order to achieve even later aspiration.

As an alternative or in addition to the program for optimising the aspiration timepoint, the system preferably has a program for optimising the aspiration speed. For example, in the case of poor synchronisation, as an alternative or in addition to shifting the aspiration timepoint it is possible for the aspiration speed to be increased or, in the case of especially good synchronisation, reduced.

The system is especially configured so that it visualises the synchronisation profile, that is to say the number of interruptions per unit time resulting from premature inhalation by the patient.

Preferably the controller has a program for operation in the case of a ventilated patient, such that, on the basis of data from the sensor, an increasing accumulation of secretions in the lung is inferred and, as a consequence, a signal for recommending tracheal aspiration is given by means of an operator interface, especially a monitor or an indicator light. In the case of a ventilated patient, the formation of secretions in the airways is challenging because the secretions must be repeatedly aspirated in order to avoid blockage of the airways/lung, but a suitable timepoint for that procedure is not easy to determine. The system according to the invention is able to detect an increasing accumulation of secretions, for example, by a change in the pressure profiles in the region of the flexible hose from cycle to cycle while the pump activity remains the same, because the accumulation of secretions gives rise to a blockage and accordingly produces a throttle effect in the flexible hose. "Cycle" here means the breathing cycle of the patient. The detection of the pressure profiles is especially carried out using the above-mentioned high-pressure sensor. The program can especially be configured so that the signal for recommending tracheal aspiration is not given until a certain number or frequency of attempts to blow out the flexible hose as described above have taken place.

In a preferred embodiment, the system is configured in such a way that by means of the pump unit a stream of gas having a discontinuous, especially pulsed, pressure profile can be generated at the patient-side end of the flexible hose. As a result, a discontinuous stream of gas can be delivered to the patient's lung, which can serve on the one hand for improving the gas exchange in the lung and on the other hand for mobilising secretions in the airways.

The system is especially configured in such a way that the pump unit is able to generate a discontinuous pressure profile such that the pressure drops from time to time in such a way that, for a brief period, suction is carried out instead of pumping. As a result, especially strong pressure surges can be generated in the respective subsequent pumping operation.

Preferably the system has a program having modi selectable by the operator, wherein one of the following values or combinations of values is specified as an objective which the program aims to fulfil by automatically adapting the aspiration and pumping:

(a) $CO_2$ elimination: the objective is an operator-specified volume of $CO_2$ that is to be eliminated per unit time (what is known as "clearance"). The clearance can be determined automatically by determining the $CO_2$ content in the stream of gas in the flexible hose.
The aim is to achieve the specified objective by changing the aspirated and pumped-back volume of gas, in the case of a piston pump by changing the pump stroke volume. The lower the $CO_2$ content in the stream of gas, the greater must be the aspirated volume of gas per breath in order to obtain the same clearance.

(b) $CO_2$ target value combined with speed of adaptation: the objective is a specific $CO_2$ value, for example in the blood or in the exhaled air, but the operator additionally specifies at what speed or within what timespan the said target value is to be achieved. The approach to achieving that objective is as described under (a) but the system adapts the change in the aspirated volume of gas per breath in dependence upon the specified speed of adaptation and the clearance measured in each case, that is to say, for example, it slowly increases the aspirated volume of gas per breath. The $CO_2$ value can either be determined on the basis of the above-mentioned gas analysis sensor or, via an interface, read off continuously or intermittently from another system, for example from a transcutaneous $CO_2$ sensor or from a blood gas analysis device. Manual input by the user is also possible.

(c) Respiratory rate: the objective is an adjustable patient respiratory rate, especially a lower respiratory rate. The program approaches achieving that objective by changing the aspirated and pumped-back volume of gas per breath by increasing the volume of gas in order to lower the respiratory rate or by reducing the volume of gas in order to stimulate the respiratory rate.

(d) CO elimination: the objective is the fastest possible elimination of toxic CO by the therapeutic principle of isocapnic hyperventilation. The program detects the volume of gas for aspiration and pumping-back that is technically the maximum advisable for the respective respiratory rate. An adjustable $CO_2$ target value is then achieved primarily by the closed-loop-controlled addition of $CO_2$. This is effected via one of the air inlet and outlet valves or via a separate metering unit.

This list is not exhaustive. The program can provide further modi. In addition, for each mode it is possible to select a switch-off sequence in which preferably an automatic stepwise reduction in the aspirated and pumped-back volume of gas down to zero takes place, taking into account a maximum tolerated, adjustable increase in respiratory rate and/or $CO_2$ content, in order to support withdrawal of the patient.

Preferably the controller has a program for operation in the case of a ventilated patient, such that, on the basis of data from the sensor, increasing or decreasing synchronisation is inferred and, as a consequence, a signal for adapting the ventilation by the ventilator, especially in respect of respiratory rate and tidal volume, is given by means of an interface. The interface can be a direct electronic interface between the system and the ventilator and/or an operator interface, especially a monitor or an indicator light. In the case of an operator interface, the actual adaptation of the ventilation by the ventilator remains the responsibility of the operator.

The invention proposes a patient set for use as part of a system as described above. The patient set has the flexible hose, the pump unit and the reservoir unit and accordingly those components which can possibly become contaminated by pathogens from the patient. The patient set is especially implemented as a single-use product or at least has parts which are single-use products. The patient set can either be in the form of an unassembled kit or in the form of an at least partly preassembled kit. The patient set may also include further elements, such as the above-described junction, filters, sensors, parts of sensors or connections for sensors.

Preferably the patient set has a measuring cuvette for a gas analysis sensor. This provides a simple way of enabling a gas analysis sensor, which is expensive to produce, to be used repeatedly, that is to say for different patients. Another possibility is hygienic decoupling by means of suitable filters.

In a preferred embodiment, the patient set has a piston pump as pump unit and reservoir unit. The piston pump has a piston which is surrounded by a cylindrical pipe. The piston has at least two ring seals for sealing with respect to the cylindrical pipe. As a result, a region that is filled with aspirated air can be rigorously separated from a region that comes into contact with environmental air. For that purpose the piston is always allowed to move relative to the cylindrical pipe only to the extent that the displacement paths do not overlap. In other words, there is no internal section of the cylindrical pipe over which both ring seals pass. As a result, pathogens or particles are prevented from being transferred in both directions. In order to ensure this and at the same time achieve a compact structure, the distance between the ring seals is preferably greater than a third, especially greater than half, of the length of the chamber for the piston in the cylindrical pipe.

Particularly in the case of the ventilated patient, the invention proposes a patient set in which the pump unit and the reservoir unit are formed by a piston pump, and the patient set has a further piston pump for forming a further pump unit and a further reservoir unit. The two piston pumps are connected to one another in fixed position relative to one another to form a kit, which need not be, but can be, in one piece. In order to ensure that the piston pumps are correctly inserted into a unit having the drives for the piston pumps, the invention provides that the kit is asymmetrical at least in respect of two main planes. The main planes are to be understood as being the orthogonal planes generated by the piston longitudinal axes, with the piston longitudinal axes especially lying in one of those planes. In other words, the kit is asymmetrical in such a way that, by means of a complementary receptacle, the two piston pumps cannot be fitted into the receptacle the wrong way round. In particular, the kit is not mirror-symmetrical in respect of a plane joining the piston longitudinal axes and/or a plane perpendicular thereto.

In the case of a system having only one piston pump, the invention preferably provides a patient set wherein the pump unit and the reservoir unit are formed by a piston pump that is asymmetrical at least in respect of two main planes. As a result, a defined position and orientation relative to the drive unit can be ensured. This is helpful, for example, when additional elements, such as identification markings, have been applied to the piston pump.

The invention is explained below with reference to an exemplary embodiment. In the drawing:

BRIEF DESCRIPTION OF THE DRAWINGS

FIG. 2 is a diagrammatic view of the system according to the invention being used in the case of a ventilated patient;

FIG. 3 is a perspective view of a grommet of the system according to the invention in a perspective view;

FIG. 4 is a perspective view of a second connector of the system according to the invention;

FIG. 4a is an enlarged view corresponding to the detail I from FIG. 4; and

DETAILED DESCRIPTION OF THE INVENTION

Figure 1:
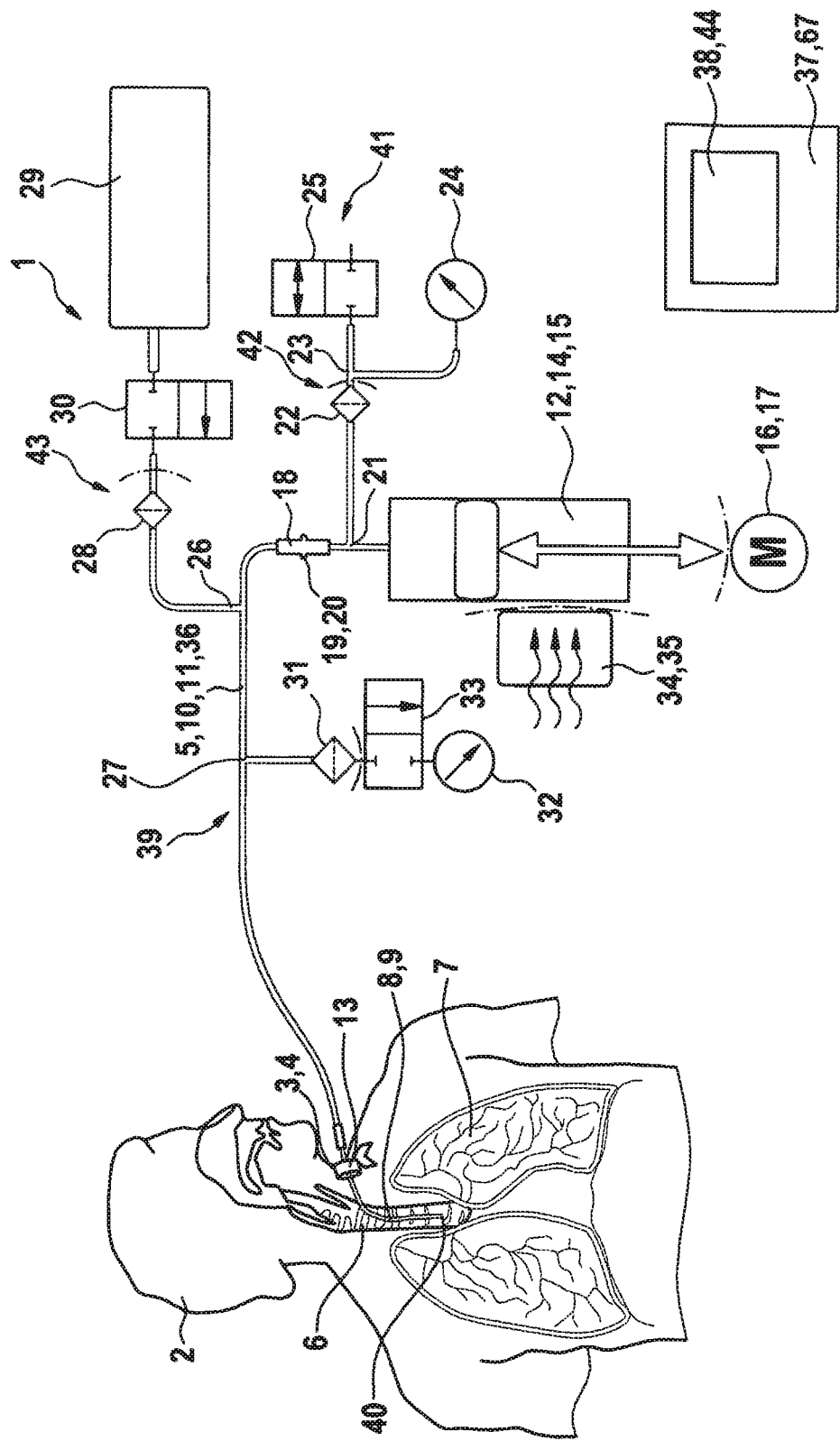
FIG. 1 is a diagrammatic view of the system according to the invention being used in the case of a non-ventilated patient.

FIG. 1 shows a diagrammatic overview of the system 1 according to the invention being used in the case of a non-ventilated patient 2. A flexible hose 5 of the system 1 has been introduced from the outside into the trachea 6 of the patient 2 through an opening 3 created by means of a small surgical intervention in the region of the throat 4 of the patient 2 and extends to a point close to the lung 7 of the patient 2. The flexible hose 5 consists of a first hose section 8 in the form of a catheter 9 for introduction into the trachea 6 and a second hose section 10 in the form of a connecting hose 11 for connection of the first hose section to a reservoir unit 12 of the system 1. The connecting hose 11 has a larger external cross-section than the catheter 9. In the region of the opening 3 the catheter 9 is surrounded by a grommet 13 and is thereby held clamped against displacement along the catheter 9. The grommet 13 is shown in greater detail in FIG. 2.

The reservoir unit 12 is in the form of a piston pump 14 and is accordingly at the same time the pump unit 15. The piston pump 14 is driven by a linear motor 16 as drive unit 17. The drive unit 17 is shown only symbolically in FIG. 1. The drive unit 17 will be described in greater detail hereinbelow with reference to FIG. 5.

The connecting hose 11 is interrupted by a measuring cuvette 18 for a gas analysis sensor 19, here a $CO_2$ sensor 20, which is attached to the measuring cuvette 18. Between the measuring cuvette 18 and the piston pump 14, the connecting hose 11 is also interrupted by a first branch 21. That first branch 21, like each of the subsequent branches, is formed by a T-piece or Y-piece. The first branch 21 leads via a first filter 22, which, like the filters described below, forms a hygienic barrier, to a second branch 23, to one outlet of which a high-pressure sensor 24 is connected and to the other outlet of which an air inlet and outlet valve 25 with an outlet to the environment is connected. Between the measuring cuvette 18 and the catheter 9, the connecting hose 11 is interrupted in succession by a third branch 26 and a fourth branch 27. The third branch 26 leads via a second filter 28 to a pressure container 29 which can be fluidically connected or separated by means of a metering valve 30. The pressure container 29 contains a therapeutic gas, especially oxygen. The fourth branch 27 leads via a third filter 31 to a high-resolution pressure sensor 32 having a sensor protection valve 33. While the high-pressure sensor 24 is designed for measuring pressures in the range of from −750 mbar to +750 mbar and therefore serves for monitoring the aspiration and pump pressures of the piston pump 14, the high-resolution pressure sensor 32 is designed for measuring pressures in the range of from −5 mbar to +5 mbar and therefore serves for monitoring the breathing of the patient 2 when the piston pump 14 is not operating. The piston pump 14 is heatable by a thermoelectric heating element 34 as temperature-control unit 35. In addition, the flexible hose 5 is encased in thermal insulation 36.

The sensors, that is to say the gas analysis sensor 19, the high-pressure sensor 24 and the high-resolution pressure sensor 32, and the actuators, that is to say the linear motor 16, the heating element 34, the air inlet and outlet valve 25, the metering valve 30 and the sensor protection valve 33, are each connected via electrical lines (not shown for clarity of the drawing) to a controller 37. The controller 37 comprises especially an input and output unit in the form of a touch-sensitive display 38, what is known as a touch screen, for operation by a user.

The flexible hose 5 and the piston pump 14, together with the first, third and fourth branches 21, 26, 27 and the three filters 22, 28, 31 and the measuring cuvette 18, constitute a patient set 39. The interfaces to the remaining components of the system 1 are each symbolised by dot-dashed lines, with customary hose connections in the form of push-fit or screw connections (not shown in detail) being used as interfaces in the region of the filters 22, 28, 31. In order to exclude incorrectly performed connection, the hose connections are mechanically coded, that is to say only the correct components fit together. Alternatively or in addition, electronic coding, such that the controller automatically recognises correct connection, would also be possible. This could be realised, for example, by RFID elements in the hose connections. The interfaces in the region of the piston pump 14 are especially of a mechanical nature, it also being possible here additionally or alternatively for electronic checking to take place. The patient set 39 is designed as a single-use product, which does not exclude the possibility of individual components being prepared, that is to say especially cleaned and sterilised, for repeated use.

The functioning of the system 1 is described hereinbelow: an open end 40 of the catheter 9 establishes a fluidic connection to the lung-side portion of the trachea 6. As a result, the breathing activity of the patient 2 can be determined via the high-resolution pressure sensor 32. In normal operation, gas is aspirated by means of the piston pump 14 at the end of the exhalation phase, that is to say end-expiratorily, and pumped back again at the end of the next inhalation phase, i.e. at the beginning of the next exhalation phase. That gas is rich in $CO_2$ and can therefore be referred to as "spent air". The aspiration and return by pumping has the effect that even during aspiration fresh air flows through the free upper airways (nose and mouth) into the trachea 6 of the patient 2 and during the subsequent inhalation process it is not spent air that first enters the lung but immediately oxygen-rich and low-$CO_2$ air, that is to say "fresh air". As a result, the $CO_2$ clearance in the lung and the uptake of $O_2$ are significantly improved. The return of the spent air has the advantage that the moisture and energy balance of the airways is not adversely affected, because no moisture and no energy are removed or supplied. In order that this water vapour is not deposited as condensate and, in addition, the system 1 does not exert an undesirable cooling effect on the patient 2, the pumped-out gas is kept warm by means of the heating element 34 during intermediate storage in the piston pump and, furthermore, heat exchange with the environment is kept low by the thermal insulation 36 or active heating of the flexible hose 5. The pump speed is especially closed-loop-controlled by means of the data from the high-pressure sensor 24. Should it be evident to the controller, for example from the pressure profiles during aspiration and pumping, that the catheter 9 is blocked, the system can blow out the blockage automatically. For that purpose, the air inlet and outlet valve 25 can be opened during aspiration, with the result that predominantly gas from the environment is drawn in. The first filter 22 ensures that there is no contamination with pathogens from the environment. After aspiration, the air inlet and outlet valve 25 is closed and the gas in the piston pump 14 is pumped out therefrom. Especially by means of discontinuous, pulse-like pumping it is possible to unblock the catheter 9 again. The air inlet and outlet valve 25 accordingly forms a switchable opening 41 to the environment, and the first branch 21 together with the second branch 23 forms a junction 42 for the switchable opening 41. The air inlet and outlet valve 25 can also be utilised to discharge some or all of the aspirated gas into the environment. Instead of or in addition to the aspirated gas it is then possible, via an opening of the metering valve 30, for a therapeutic gas to be conducted from the pressure container 29 to the patient 2 via the flexible hose 5, it also being possible for that purpose for the pumping operation to be shifted in time, especially into the inhalation phase of the patient 2. The third branch 26 together with the metering valve 30 forms a switchable supply line 43 through which a volumetric flow of a further gas can be conducted to the flexible hose 5 instead of or in addition to the recirculated gas.

The mentioned functions are controlled automatically by the controller 37 in dependence upon inputs by the operator on the one hand and the data from the sensors, that is to say the gas analysis sensor 19, the high-pressure sensor 24 and the high-resolution pressure sensor 32. The touch-sensitive display 38 serves as a user interface 44. In addition, the controller 37 can be used to select and operate the modi described in the general part. The same applies to the above-described functionality of the controller 37 for the ventilated patient, still to be discussed below. To avoid repetition, these functions of the controller 37 will not be discussed again.

FIG. 2 shows the situation in the case of a ventilated patient 2; here the same reference numerals are used for the same or at least similar components and, to avoid repetition, only the differences with respect to the situation in FIG. 1 will be discussed below. Unlike FIG. 1, the switchable supply line 43 and the high-resolution pressure sensor 32 are not shown because those components are not generally used in the case of a ventilated patient 2. They can nevertheless be present however. In the case of a ventilated patient the catheter 9 is passed into the trachea 6 not through a separate opening in the throat 4 of the patient 2 but usually through a hose-like tube 45 which is part of a line system 46 of a ventilating system 47.

The ventilating system 47 has a central unit 48 having a pump, controller, user interface and the like, the details of which are not important here. Two ventilation hoses 49 extend from that central unit 48 as far as a Y-piece 50 which is followed in succession by a first connector 51, a filter element 52 with HME (Heat and Moisture Exchanger), a hose-like tube extension 53 and finally a second connector 54. The tube 45 is connected to the second connector 54, which is not described in detail below. The ventilating system 47 operates in known manner, that is to say air, oxygen and/or therapeutic gases are pumped into the lung 7 of the patient 2 via a ventilation hose 49, the tube 45 and the intermediately located components and, in alternation therewith, the spent air is discharged again in the reverse direction but via the other ventilation hose 49. The ventilation hoses 49, together with the tube 45 and the intermediately located components, form the line system 46 of the ventilating system 47. Of course, here it is also possible to imagine other ventilators that have only one ventilation hose and, for example, a patient-side valve system or leakage system.

A further flexible hose 55 is connected to the first connector 51. This further flexible hose 55 serves for connection to a further piston pump 56 which forms a further pump unit 57 and a further reservoir unit 58. The further piston pump 56 is driven by means of a further linear motor 59. The piston pump 56 is assigned a further temperature-control unit 60 and, via a junction and a filter, a further high-pressure sensor 61 and a further air inlet and outlet valve 62 are connected. While the above-described flexible hose 5 with the elements connected thereto, such as the piston pump 14, forms a first pathway 63, the further flexible hose 55 with the elements connected thereto, such as the further piston pump 56, forms a second pathway 64. The second pathway 64 does not have a measuring cuvette, but this is not excluded, for example if the $CO_2$ concentration in that region is to be measured. Especially the further flexible hose 55 and the further piston pump 56 are part of the patient set 39, the interfaces to the remaining components of the system 1 being of analogous construction to the first pathway 63 and again being each symbolised by dot-dashed lines.

Also connected to the first connector 51, as part of the patient set 39, is a third flexible hose 65 which is connected via a filter to a ventilation pressure sensor 66. The ventilation pressure sensor 66 has a measuring range of +/−100 mbar. The further high-pressure sensor 61 and the ventilation pressure sensor 66 are arranged on the connector 51 offset with respect to one another in the flow direction of the ventilating system 47. At least as long as the further piston pump 56 is not moving, the direction of flow and flow velocity in the first connector 51 and accordingly in the line system 46 of the ventilating system 47 can be inferred by way of measurement of the pressure differential by the mentioned sensors. This allows the system 1 to be synchronised with the ventilating system 47.

The components of the second pathway 64 and the third ventilation pressure sensor 66 are also connected to the controller 37.

The two pathways 63, 64 support the ventilation of the patient 2, which is essentially carried out by the ventilating system 47 by alternately effecting pumping-out and return by means of the two piston pumps 14, 56. At the end of exhalation, spent breathing gas is extracted from the airways 7 by the first pathway 63, while at substantially the same time fresh gas is returned by the second pathway 64. In reality, the return begins slightly earlier in order that there is no reduction in pressure in the line system 46 of the ventilating system 47, which reduction in pressure would, to the ventilating system, suggest inhalation by the lung. For the slightly staggered operation of the piston pumps 14, 56 it is important that they are not rigidly coupled but are each driven independently of one another by a respective linear motor 16, 59. By means of the aspiration, the spent $CO_2$-rich gas is removed from the dead space and replaced by the fresh gas supplied via the second pathway.

The gas aspirated by the first pathway 63 is returned again at the end of the following inhalation or at the beginning of the following exhalation, while at substantially the same time fresh gas is pumped out of the ventilating system by the second pathway 64.

All the elements described above for the non-ventilated patient, such as the optional discontinuous movement of the piston pump, are also retained in this configuration for the ventilated patient, as are, for example, the above-described programs.

The system 1 has a communication interface 67 in the region of the controller 37. This consists of both a connection (not shown in detail) for a cable connection and a WLAN or Bluetooth interface such that an exchange of information with third-party devices, with external sensors and/or with remote monitoring systems can take place both via a cable connection and wirelessly. In particular, the system can be coupled to the ventilating system 47.

Individual components of the system 1 will be described in greater detail below. FIG. 3 shows the grommet 13. The grommet 13 consists of two parts, firstly a main body 68 and secondly a clamping collar 69. Both parts are substantially rotationally symmetrical. The main body 68 has a tubular piece 70 between a rear and a front flange 71, 72, the front flange 72 being approximately twice as large in diameter as the rear flexible flange 71. On the other side of the front flange 72, the tubular piece 70 merges into a clamping piece 73 having four slots, which clamping piece has an external thread 74 and a conically tapering end 75. The clamping collar 69 is sleeve-like and has an internal thread 76 which matches the external thread 74 and is adjoined by a portion 77 that tapers conically in diameter. For ease of handling, the clamping collar 69 has four longitudinal beads 78 distributed around its outer circumference. The grommet 13 can be introduced, rear flange 71 first, into the opening 3 in the throat 4 of the patient 2. The rear flange 71 prevents the grommet 13 from unintentionally slipping out of the opening 3, and the front flange 72 prevents the grommet from slipping further into the opening 3. In the next step the catheter 9 is pushed through the clamping collar 69 and the main body 68 into the trachea 6. As soon as the catheter 9 has been pushed in sufficiently far, that position is fixed by clamping the catheter 9 in the grommet 13. For that purpose the clamping collar 69 is screwed onto the clamping piece 73. The conically tapering end 75, the tapering-diameter portion 77 and the slotting of the clamping piece 73 together have the effect of compressing the clamping piece 73 radially, with the result that the catheter 9 is clamped in place.

FIG. 4 and FIG. 4a show the second connector 54. This has a tube-like connector main body 79, the first, open end of which has a tube connection 80 and the other end of which has a duckbill valve 81 for introduction of a single-use aspiration catheter (not shown) for aspiration of secretions. On a radial side, the connector main body 79 has a first connecting socket 82 for the tube extension 53, the Figures showing that the tube extension 53 is a hose reinforced by means of a coil 83. Radially opposite the connecting socket 82, the connector main body 79 has a catheter connection 84 that points obliquely away from the tube connection 80. The catheter 9, which has a protective cover system 85, is connected to the catheter connection 84. The protective cover system 85 includes a clamping sleeve 86, with which, by axial displacement, the catheter connection 84 can be made radially narrower, and a protective cover 87 in the form of a tubular film connected to the clamping sleeve 86. The opposite end of the tubular film ends at a connecting piece 88 which is also part of the protective cover system 85 and in which the catheter 9 is fixed in place. The connecting hose 11 is attached on the opposite side, so that the connecting piece 88 forms the connection between the connecting hose 11 and the catheter 9. FIGS. 4 and 4a show the state in which the catheter has been fully withdrawn from the tube 45, for example in order to aspirate secretions with an aspiration catheter. The catheter 9 is protected from contamination by the protective cover system 85 and, after the aspiration, can be guided into the tube 45 again through the second connector 54, the protective cover 87 being axially compressed. By displacement of the catheter connection 84, the catheter 9 is clamped in place and thus secured against unintentional displacement.

Such a protective cover system can also be provided in the variant for non-ventilated patients in the region of the grommet 13.

Figure 5:
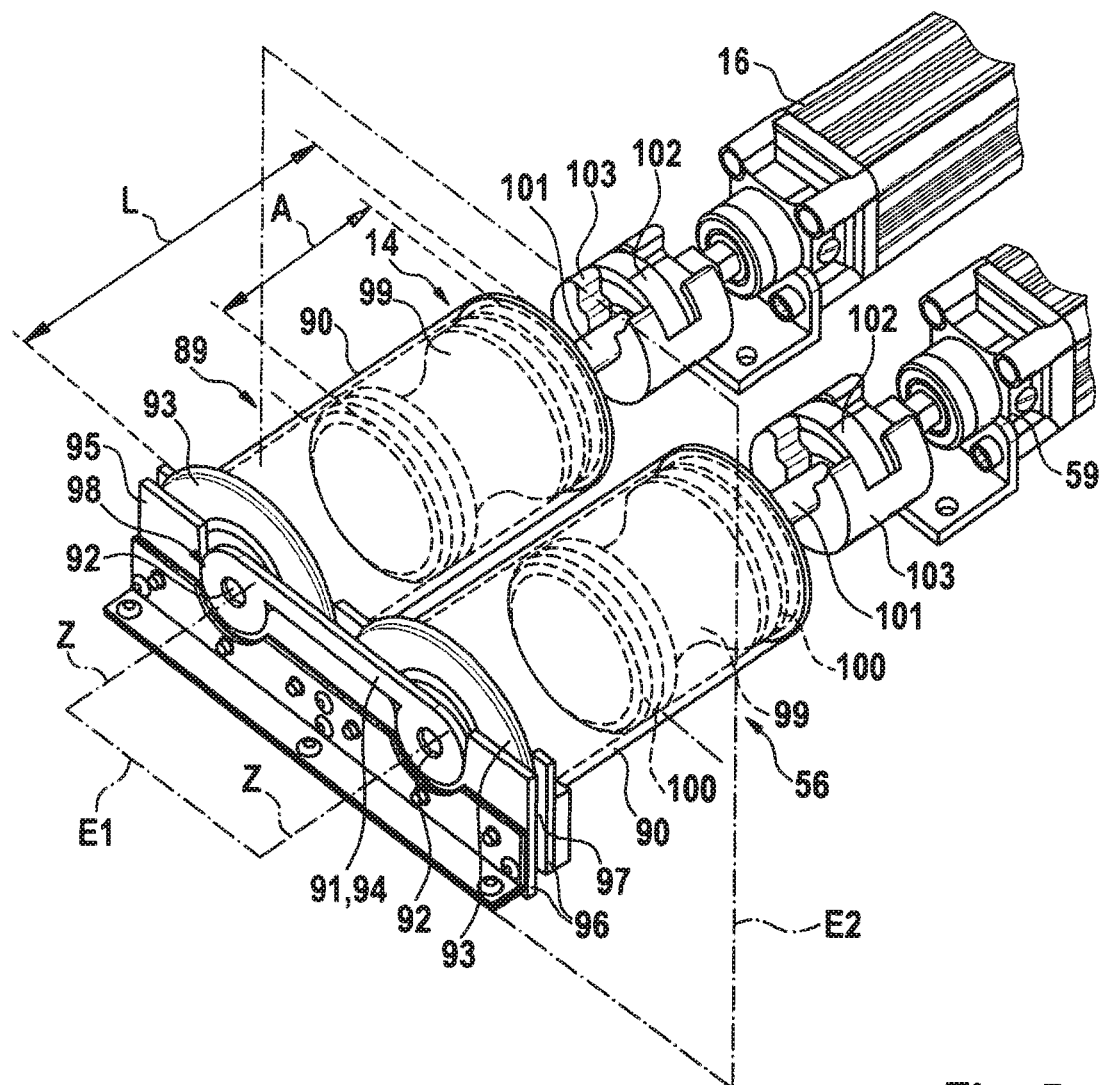
FIG. 5 is a perspective view of a kit according to the invention comprising two piston pumps with their receptacle and drive units.

FIG. 5 shows the arrangement of the piston pump 14 and the further piston pump 56 in the form of a kit 89 having the associated linear motor 16 and the further linear motor 59. The two piston pumps 14, 56 each have a transparent cylindrical pipe 90 which is closed towards one end by a common cylinder head 91 apart from a connection opening 92 for the flexible hose 5 and the further flexible hose 55, respectively. The cylinder head 91 connects the two cylindrical pipes 90 and thereby positions them in fixed position relative to one another, the longitudinal axes Z of the cylindrical pipes 90 being parallel to one another and defining a first main plane E1 of the kit 89. The cylinder head 91 has a circular disc 93 arranged coaxially with each cylindrical pipe 90 and, offset axially therebetween, a connecting bar 94 which, however, is offset radially with respect to the longitudinal axes Z and offset parallel to the first main plane E1. The kit 89 is accordingly not symmetrical with respect to the first main plane E1. The kit 89 is likewise not symmetrical with respect to a second main plane E2, which is perpendicular to the first main plane E1 and to the longitudinal axes Z, because the cylinder head 91 is arranged only at one end of the cylindrical pipes 90, it being immaterial exactly where along the longitudinal axis Z that second main plane E2 is positioned. The kit 89 can be inserted with the circular discs 93 into a complementary receptacle 95 and, in accordance with the lack of symmetry, only in the intended orientation shown. For that purpose the receptacle 95 has, for the circular discs 93, a slot 97 formed by two spaced-apart sheet metal plates 96 and, for the connecting bar 94, a recess 98 such that the two piston pumps 14, 56 cannot be fitted into the receptacle 95 the wrong way round. A piston 99 is arranged in each cylindrical pipe 90. The pistons 99 each have a circumferential ring seal 100 at their ends. The distance A between the ring seals 100 corresponds to approximately half of a length of the chamber for the piston 99 in the respective cylindrical pipe 90. This ensures that the longitudinal regions over which the ring seals 100 pass do not overlap and in neither direction is there any contamination between the interior of the piston pumps 14, 56 and the environment. At their ends remote from the cylinder head 91 the pistons 99 are each lengthened by a piston rod 101 having a rotationally symmetrical, disc-shaped grip piece 102. The grip pieces 102 are each snapped radially into a claw 103 which is connected to the respective linear motor 16, 59. The claw 103 has for that purpose a counter-contour complementary to the grip piece 102. The counter-contour is configured so that it engages around the grip piece 102 over slightly more than half its circumference, so that the grip piece can be snapped into place. Accordingly, the piston pumps 14, 56 forming the pump units 15, 57 can be coupled to and separated from the linear motors 16, 59 forming the drive units without tools.

LIST OF REFERENCE SIGNS 1 system
2 patient
3 opening
4 throat
5 flexible hose
6 trachea
7 lung
8 first hose section
9 catheter
10 second hose section
11 connecting hose
12 reservoir unit
13 grommet
14 piston pump
15 pump unit
16 linear motor
17 drive unit
18 measuring cuvette
19 gas analysis sensor
20 $CO_2$ sensor
21 first branch
22 first filter
23 second branch
24 high-pressure sensor
25 air inlet and outlet valve
26 third branch
27 fourth branch
28 second filter
29 pressure container
30 metering valve
31 third filter
32 high-resolution pressure sensor
33 sensor protection valve
34 heating element
35 temperature-control unit
36 thermal insulation
37 controller
38 touch-sensitive display
39 patient set
40 open end of the flexible hose 5
41 switchable opening to the environment
42 junction for the switchable opening 41
43 switchable supply line
44 user interface
45 tube
46 line system of the ventilating system 47
47 ventilating system
48 central unit of the ventilating system 47
49 ventilation hose
50 Y-piece
51 first connector
52 filter element
53 tube extension
54 second connector
55 further flexible hose
56 further piston pump
57 further pump unit
58 further reservoir unit
59 further linear motor
60 further temperature-control unit
61 further high-pressure sensor
62 further air inlet and outlet valve
63 first pathway
64 second pathway
65 third flexible hose
66 ventilation pressure sensor
67 communication interface
68 main body of the grommet 13
69 clamping collar of the grommet 13
70 tubular piece of the main body 68
71 rear flange of the main body 68
72 front flange of the main body 68
73 clamping piece of the main body 68
74 external thread of the clamping piece 73
75 end of the clamping piece 73
76 internal thread of the clamping collar 69
77 tapering-diameter portion of the clamping collar 69
78 longitudinal bead of the clamping collar 69
79 connector main body 80 tube connection
81 duckbill valve
82 connecting socket for the tube extension 53
83 coil
84 catheter connection
85 protective cover system
86 clamping sleeve
87 protective cover
88 connecting piece
89 kit
90 cylindrical pipe
91 cylinder head
92 connection opening
93 circular disc
94 connecting bar
95 receptacle
96 sheet metal plate
97 slot
98 recess
99 piston
100 ring seal
101 piston rod
102 grip piece
103 claw
A distance between the ring seals 100
E1 first main plane of the kit 89
E2 second main plane of the kit 89
L length of the chamber for the piston 99 in the cylindrical pipe 90
Z longitudinal axis of the cylindrical pipe 90

The invention claimed is:

1. A system for supporting pulmonary gas exchange in patients and for at least one of coupling to a ventilating system or use in the case of non-ventilated patients, which has a flexible hose introducible into the trachea of a patient, a pump unit, a reservoir unit and a controller such that via the flexible hose and by means of the pump unit it is possible to regulate aspiration, and recirculation, of the aspirated gas, wherein the system has a sensor having an output based on which the controller is configured to control timing of the pump unit to initiate aspiration of gas during exhalation by the patient in order to be stored in the reservoir unit, and recirculation of the aspirated gas from the reservoir unit during subsequent inhalation or exhalation by the patient, and wherein based on the output of the sensor the controller causes the aspiration of gas to be initiated end-expiratorily, and the recirculation to be initiated late-inspiratorily or early expiratorily.

2. The system according to claim 1, wherein the sensor is a high-pressure sensor which is configured and arranged in such a way that it is able to detect the fluctuations in pressure generated by the pump unit.

3. The system according to claim 1, wherein the sensor is a high-resolution pressure sensor for detecting breathing activity on the basis of fluctuations in pressure in the flexible hose generated by spontaneous breathing of the patient.

4. The system according to claim 1, wherein the flexible hose has a first hose section for introduction into the trachea and a second hose section for connection of the first hose section to the reservoir unit with a larger external cross-section.

5. The system according to claim 1, wherein the system has a further flexible hose, a further pump unit and a further reservoir unit for aspirating and recirculating gas from the line system of a ventilating system.

6. The system according to claim 5, wherein the pump unit and the further pump unit are controllable independently of one another by the controller.

7. The system according to claim 1, wherein a $CO_2$ sensor is arranged between an open end of the flexible hose and the reservoir unit in respect of the flow of the gas conducted by the system.

8. The system according to claim 1, wherein the system has a junction with a switchable opening to the environment, to the ventilation circuit or to an external gas source such that, by means of the pump unit, gas can be drawn in therefrom, or the inflow of gas is made possible, for blowing out the flexible hose in the event of a blockage.

9. The system according to claim 1, wherein the pump unit is couplable to and separable from a drive unit for the pump unit by the user without tools.

10. The system according to claim 1, wherein the system has a grommet for passing-through and fixing of the flexible hose in a surgically created opening in the trachea and for keeping that opening open.

11. The system according to claim 1, wherein the controller is configured in such a way that, in dependence upon data from the sensor and/or inputs via a user interface, closed-loop control and/or an output with at least one of the following output variables takes place: velocity profile of the pumping/aspiration, pumped/aspirated volume.

12. The system according to claim 1, wherein the system is configured in such a way that by means of the pump unit a stream of gas having a discontinuous pressure profile can be generated at the patient-side end of the flexible hose.

13. A patient set for use as part of a system for supporting pulmonary gas exchange in patients and for at least one of coupling to a ventilating system or use in the case of non-ventilated patients, which has a flexible hose introducible into the trachea of a patient, a pump unit, a reservoir unit and a controller such that via the flexible hose and by means of the pump unit it is possible to regulate aspiration, and recirculation, of the aspirated gas, wherein the system has a sensor having an output based on which the controller is configured to control timing of the pump unit to initiate aspiration of gas during exhalation by the patient in order to be stored in the reservoir unit, and recirculation of the aspirated gas from the reservoir unit during subsequent inhalation or exhalation by the patient, wherein the patient set includes the flexible hose, the pump unit and the reservoir unit, and wherein based on the output of the sensor the controller causes the aspiration of gas to be initiated end-expiratorily, and the recirculation to be initiated late-inspiratorily or early expiratorily.

14. The patient set according to claim 13, wherein the patient set has a measuring cuvette for a gas analysis sensor.

15. The patient set according to claim 13, wherein the pump unit and the reservoir unit are formed by a piston pump having a piston which is surrounded by a cylindrical pipe, and the piston has at least two ring seals for sealing with respect to the cylindrical pipe.

16. The patient set according to claim 13, wherein the pump unit and the reservoir unit are formed by a piston pump; the patient set has a further piston pump for forming a further pump unit and a further reservoir unit for aspirating and recirculating gas from the line system of a ventilating system; and the piston pump and the further piston pump are connected to one another in fixed position relative to one another in the form of a kit; and the kit is asymmetrical at least in respect of two main planes.

* * * * *